United States Patent [19]
Salomon

[11] Patent Number: 4,915,858
[45] Date of Patent: * Apr. 10, 1990

[54] NITROGEN CONTAINING ANTI-OXIDANT COMPOSITIONS

[75] Inventor: Mary F. Salomon, Cleveland Heights, Ohio

[73] Assignee: The Lubrizol Corporation, Wickliffe, Ohio

[*] Notice: The portion of the term of this patent subsequent to Jan. 17, 2006 has been disclaimed.

[21] Appl. No.: 210,603

[22] Filed: Jun. 23, 1988

Related U.S. Application Data

[63] Continuation of Ser. No. 59,884, Jun. 9, 1987, Pat. No. 4,798,684.

[51] Int. Cl.$^4$ .......................................... C10M 135/22
[52] U.S. Cl. .................. 252/47.5; 252/49.3; 252/78.1; 252/402; 568/44; 568/57
[58] Field of Search ................ 252/47.5, 78.1, 402; 568/44, 57

[56] References Cited

U.S. PATENT DOCUMENTS

| | | | |
|---|---|---|---|
| 2,282,710 | 5/1942 | Dietrich | 252/47 |
| 2,350,746 | 6/1944 | Fuller | 252/47 |
| 2,467,713 | 11/1944 | Watkins | 252/42.7 |
| 2,781,318 | 2/1957 | Cuphers | 252/47 |
| 2,914,527 | 11/1959 | Winthrop | 544/38 |
| 3,156,728 | 11/1964 | Orloff et al. | 252/47 X |
| 3,175,974 | 3/1965 | Rai et al. | 252/47 |
| 3,224,972 | 12/1965 | Orloff et al. | 252/47 |
| 3,344,068 | 9/1967 | Waight et al. | 252/47.5 |
| 3,376,224 | 4/1968 | Elliott et al. | 252/47.5 |
| 3,399,041 | 8/1968 | McCabe | 44/73 |
| 3,536,706 | 10/1970 | Randell | 252/47 X |
| 3,560,531 | 2/1971 | Normanû260 | 389/ |
| 3,803,140 | 4/1974 | Cook et al. | 544/35 |
| 4,031,023 | 6/1977 | Musser et al. | 252/48.2 |
| 4,177,153 | 12/1979 | Lowe | 252/32.7 E |
| 4,659,490 | 4/1987 | Louthan et al. | 252/47.5 |
| 4,798,684 | 1/1989 | Salomon | 252/47.5 |

FOREIGN PATENT DOCUMENTS

| | | |
|---|---|---|
| 0233140 | 8/1987 | European Pat. Off. |
| 1066019 | 9/1958 | Fed. Rep. of Germany |
| 3426367 | 1/1986 | Fed. Rep. of Germany |
| WO88/02007 | 3/1988 | PCT Int'l Appl. |

OTHER PUBLICATIONS

Woodward, "Thioglycol Polymers. I. Hydrochloric Acid-Catalyzed Autocondensation of Thiodiglycol", Journal of Polymer Science 1959, vol. XLI, pp. 219–223.

Johnson, "Improvements in Retarding the Oxidation of Substances Sensitive to Oxidation" Dec. 1938.

Cole et al., "Antioxidant Mechanism Studies of the Phenothiazine Types", Sep. 1956.

*Primary Examiner*—William R. Dixon, Jr.
*Assistant Examiner*—E. McAvoy
*Attorney, Agent, or Firm*—Forrest L. Collins; Frederick D. Hunter; Robert A. Franks

[57] ABSTRACT

This invention describes compositions containing nitrogen, sulfur and optionally oxygen which are useful as antioxidants for lubricants.

28 Claims, No Drawings

NITROGEN CONTAINING ANTI-OXIDANT COMPOSITIONS

This is a continuation of co-pending application Ser. No. 07/059,884 filed on 9 June 1987, now U.S. Pat. No. 4,798,684.

BACKGROUND OF THE INVENTION

Field of the Invention

This invention relates to antioxidants which contain nitrogen, sulfur and optionally oxygen atoms. The compositions are particularly useful in lubricant compositions for their antioxidant ability. In U.S. Pat. No. 2,282,710 to Dietrich issued May 12, 1942 it is known that stabilization of petroleum hydrocarbons against the deleterious catalytic action of metals may be obtained by compositions containing both a nitrogen and a sulfur functional group. Various cyclic, aromatic and linear carbon configurations are shown in the sulfur and nitrogen containing molecules of Dietrich. Dietrich discloses preparing his compositions by the use of ethyleneimine. Dietrich further states that his compounds are particularly effective in retarding the formation of products corrosive to metals, and particularly cadmium, silver, copper, lead and like bearing alloys under normal service conditions.

German OLS 1,066,019 published Sept. 24, 1959 by Holtschmitt et al describes various condensation products of thioglycol and nitrogen containing materials. Holtschmitt shows his compounds as containing free hydroxyl groups. Holtschmitt further discloses the use of aromatic amines containing a short aliphatic group on the aromatic ring, e.g. toluidine.

It is known from an article entitled *Thioglycol Polymers I Hydrochloric Acid-Catalysed Auto Condensation of Thiodiglycol* by Woodward, Journal of Polymer Science the OL XLI, Pages 219-223 (1959), that the properties of a sulfur and oxygen containing compound allow end-to-end condensation. It is further known from the Woodward article that multiple sulfur linkages within the molecule, e.g. disulfides, trisulfides, and the like may be obtained.

It is further known that various amines may be utilized in antioxidant compositions. Phenothiazine compounds are known in lubricant products from U.S. Pat. No. 2,781,318 issued Feb. 12, 1957 to Cyphers. The alkyl phenothiazines of Cyphers are alkylated on the phenylene rings of the phenothiazine structure. Cyphers does not show or suggest the alkylation of the amine nitrogen in phenothiazine. The Cyphers patent is directed to the utility of phenothiazine as an antioxidant and corrosion inhibiting additive for ester, polyester, polyether and other synthetic lubricants.

U.S. Pat. No. 3,536,706 issued Oct. 27, 1970 to Randell suggests that phenothiazines may be used as additives for synthetic lubricants. The phenothiazines particularly described by Randell are those containing tertiary alkyl substituents having from 4 to 12 carbon atoms on the aryl groups which make up the phenothiazine structure. Randell also discloses fused rings on the two phenylene groups which make up the phenothiazine structure. Stated otherwise, Randell allows the utilization of naphthalene for at least one of the two aryl groups in the phenothiazine structure.

U.S. Pat. No. 3,803,140 issued to Cook et al on Apr. 9, 1974 describes various tertiary alkyl derivatives of phenothiazine. N-alkyl substitution or N-alkenyl substitution is described on the phenothiazine structure. Ring alkylation when the phenothiazine is in the free nitrogen form is also shown. Cook et al express a preference for non-N substituted phenothiazine derivatives.

Cook et al also suggest that organic materials which are susceptible to oxidative degradation may benefit through the use of the compounds of their invention. Such uses include antioxidants for aliphatic hydrocarbons such as gasoline, lubricating oils, lubricating greases, mineral oils, waxes, natural and synthetic polymers such as rubber, vinyl, vinylidene, ethers, esters, amides and urethanes. The compounds of Cook et al are also suggested for stabilizing aldehydes and unsaturated fatty acids or esters thereof. Still further utilities suggested by Cook et al include the stabilization of organometalloid substances such as silicone polymers. Another class of uses of the compounds of Cook et al include the stabilization of vitamins, essential oils, ketones and ethers.

Normant in U.S. Pat. No. 3,560,531 issued Feb. 2, 1971, describes metallation of materials having active hydrogens including phenothiazine. U.S. Pat. No. 3,344,068 issued Sept. 26, 1967, to Waight et al describes antioxidants for ester-based lubricants. Waight et al's compounds have an N-hydrocarbyl substituted phenothiazine structure. The N-substituted phenothiazine compounds of Waight et al are also substituted in at least one position on the fused aromatic nuclei. A second required component in the compositions of Waight et al is a secondary aromatic amine having two aromatic groups attached to the nitrogen atom.

The preparation of alkylthioalkanols which are useful as intermediates for preparing the compounds of the present invention are described in U.S. Pat. No. 4,031,023 to Musser et al. The Musser et al patent was issued June 21, 1977 and is assigned to The Lubrizol Corporation.

U.S. Pat. No. 2,194,527 to Winthrop et al which issued Nov. 24, 1959, describes pharmaceutical compounds such as omega-(10-phenothiazinyl)alkyl di-alkyl sulfonium salts which are useful as spasmolytics and in particular antihistaminics. U.S. Pat. No. 3,376,224 issued Apr. 2, 1968 to Elliott et al describes phenothiazine derivatives which are stated to be N-substituted methylene compounds which contain an ether linkage between the methylene group and an alkyl or cycloalkyl radical. According to Elliott et al, the alkyl or cycloalkyl radical may carry an alkoxy or other non-reactive substituent.

It has been found in the present invention that particularly effective antioxidant compositions may be obtained through the inclusion of a nitrogen functionality from an amine, and an oxygen and sulfur functionality from a compound such as a beta-thiodialkanol. Of course, within the present invention other methods of preparing the claimed compounds will be apparent.

Throughout the specification and claims percentages and ratios are by weight, temperatures are in °C., and pressures are in KPa gauge unless otherwise indicated. To the extent that the references cited herein are applicable, they are incorporated by reference.

SUMMARY OF THE INVENTION

The present invention describes a composition of matter which is the amine terminated reaction product obtained from two equivalents of a secondary aromatic monoamine with at least two equivalents of a betathiodialkanol.

A further feature herein is a composition produced by the reaction of at least two equivalents of a primary or secondary amine or mixtures thereof containing at least one straight or branched aliphatic group of 4 or more carbon atoms, with at least two equivalents of a betathiodialkanol.

The invention also embodies a composition which is the amine terminated reaction product of two equivalents of an aliphatic ring-substituted aromatic amine with at least two equivalents of a beta-thiodialkanol.

A still further embodiment of the invention is a composition of the formula:

$$R^1R^2N(AS_xAO)_yAS_xANR^3R^4$$

wherein A is an alkylene group, x is at least one, y is 0 or greater, $R^1$, $R^2$, $R^3$ and $R^4$ are such that $R^1$ and $R^3$ are straight or branched aliphatic groups of 4 or more carbon atoms, or $R^1$ and $R^2$ are both aromatic groups and $R^3$ and $R^4$ are hydrocarbyl groups, or at least one of $R^1$ and $R^3$ is an aromatic group and at least one of $R^2$ and $R^4$ is an aliphatic group of 4 or more carbon atoms; with the proviso that any of the remaining members of $R^1$, $R^2$, $R^3$ or $R^4$ groups may be hydrogen or hydrocarbyl.

The inventions described above are useful in automatic transmission fluids and in lubricants comprising a major amount of an oil of lubricating viscosity and a minor amount of the above compositions.

DETAILED DESCRIPTION OF THE INVENTION

The first aspect of the present invention is the amine component which may be used to form the compositions of the present invention. Virtually any primary or secondary amine containing compound may be utilized in the present invention. Tertiary amine compounds are not useful herein due to their salt forming tendency and the requirement for the presence of a reactive hydrogen in order to form the necessary bonds with the later described thiodialkanol. However, tertiary amine functionality may be present within the amine molecule provided that there is at least one other reactive hydrogen in the molecule e.g. a primary or secondary amine in the molecule. The invention has several aspects, and in one aspect it is highly desired that the amine be a secondary amine and most preferably that the secondary amine is the only amine functionality in the molecule, that is, a compound as previously described would be monofunctional with respect to the number of nitrogen atoms of an amine character within the molecule.

It is also highly desired that the amine contain a hydrocarbyl group of at least one straight or branched structure of four or more carbon atoms to assist in oil-solubility or oil-dispersibility. It is preferred that the hydrocarbyl group be an aliphatic group such as a polyisobutylene or polyisopropylene.

The term hydrocarbyl is a moiety containing hydrogen and carbon and any other atoms which are noninterfering with the intent of the invention. It is further preferred that the hydrocarbyl group be a straight or branched group containing 4 or more carbon atoms, preferably from 6 to 200 carbon atoms and most preferably from 12 to 18 carbon atoms.

A highly preferred amine is phenothiazine or a phenothiazine derivative or material which contains a phenothiazine structure. Compounds having the desired phenothiazine structure are defined by the formula:

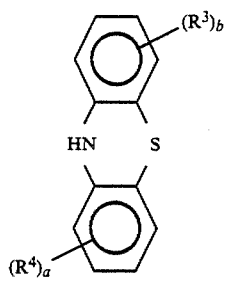

wherein $R^3$ and $R^4$ are independently alkyl, alkenyl, aryl, alkaryl, aralkyl, halogen, hydroxyl, alkoxy, aryloxy, alkylthio, arylthio, fused aromatic rings and mixtures thereof and a and b are independently greater or zero.

To obtain the derivatives of phenothiazine where (a) and (b) in formula IA are not 0, it is suggested that U.S. Pat. No. 2,781,318 to Cyphers issued Feb. 12, 1957 be consulted. A dialkyl diphenyl amine treated with sulfur at elevated temperatures, such as in the range of 145° C. to 205° C. for a sufficient time to complete the reaction, gives compounds which may be derivatized within the scope of formula I. Conveniently, a catalyst such as iodine may be utilized to establish the sulfur bridge. The reaction is essentially clean and does not affect the amine hydrogen in the composition. Typically, a dialkylated product will be obtained, e.g., where both (a) and (b) are each 1. The monoalkylated phenothiazine derivatives are conveniently obtained by utilizing a monoalkylated diphenylamine which is then cyclized to obtain the corresponding monoalkylated phenothiazine. Similarly, phenothiazine may be alkylated with olefins using a Lewis acid catalyst.

While the derivatives $R^3$ and $R^4$ have been defined above as alkyl, any hydrocarbyl group may be employed. It is convenient to utilize alkenyl, aryl, alkaryl, aralkyl, halogen, hydroxyl, alkoxy, alkylthio, arylthio and the like for $R^3$ and $R^4$. To obtain the hydroxyl derivative one would react, for example, aniline and hydroquinone to form 4-hydroxydiphenylamine which is then cyclized with sulfur. The corresponding alkoxy compounds may be obtained by reacting the hydroxy-containing phenothiazine with an alkyl halide.

Similar to obtaining the alkyl derivatives as $R^3$ and $R^4$, the alkenyl, aryl, alkaryl, aralkyl, and fused ring derivatives may be prepared. The fused ring derivatives may be prepared from phenyl naphthylamines which may be cyclized by sulfurization to produce benzophenothiazines. Moreover, the corresponding polyaromatic compounds and their alkyl derivatives are obtained in a similar fashion. The halogenated forms of the product are obtained by treatment of phenothiazine with, for example, bromine or chlorine. The values for $R^3$ and $R^4$ as alkylthio and arylthio are conveniently obtained by treatment of phenothiazine with thiourea and iron chloride. Hydrolysis of isothiuronium chloride to thiophenol which is then alkylated as previously described gives $R^3$ ($R^4$) as alkylthio.

Of course, mixtures of the varying values of $R^3$ and $R^4$ are included within the scope of the present invention. Thus, $R^3$ may be a chloro group, while $R^4$ is an alkyl group. The present invention as previously noted also allows for $R^3$ and $R^4$ to independently be different alkyl groups. That is, $R^3$ and $R^4$, while both being alkyl, can be of different carbon chain lengths. The position of $R^3$ and $R^4$ alkyl groups on the aromatic rings will typically be in the para position to the heterocyclic nitrogen, although para substitution to the heterocyclic sulfur may also occur. It is also convenient to utilize derivatives where $R^3$ and $R^4$ are independently aryl. Conveniently, $R^3$ and $R^4$ as hydrocarbyl moieties will contain from about 3 to about 30 carbon atoms in each moiety. Preferably, $R^3$ and $R^4$ as hydrocarbyls will contain independently from about 4 to about 15 carbon atoms.

Additional amines which may be employed in the present invention are those having the parameters previously listed which include the following.

The monoamines and polyamines useful are characterized by the presence within their structure of at least one H—N group. Therefore, they have at least one primary (i.e., $H_2N$—) or secondary amino (i.e., H—N=) group. The amines can be aliphatic, cycloaliphatic, aromatic, or heterocyclic, including aliphatic-substituted cycloaliphatic, aliphatic-substituted aromatic, aliphatic-substituted heterocyclic, cycloaliphatic-substituted aliphatic, cycloaliphatic-substituted heterocyclic, aromatic-substituted aliphatic, aromatic-substituted cycloaliphatic, aromatic-substituted heterocyclic, heterocyclic-substituted aliphatic, heterocyclic-substituted alicyclic, and heterocyclic-substituted aromatic amines and may be saturated or unsaturated. The amines may also contain non-hydrocarbon substituents or groups as long as these groups do not significantly interfere with the reaction of the amines with the alkylating agents. Such non-hydrocarbon substituents or groups include lower alkoxy, nitro, esters, amides, interrupting groups such as —O— and —S— (e.g., as in such groups as $-CH_2CH_2-X-CH_2CH_2-$ where X is —O— or —S—.

With the exception of the branched polyalkylene polyamine, the polyoxyalkylene polyamines, and the high molecular weight hydrocarbyl-substituted amines described more fully hereafter, the amines used ordinarily contain less than about 40 carbon atoms in total and usually not more than about 20 carbon atoms in total.

Aliphatic monoamines include mono-aliphatic and di-aliphatic substituted amines wherein the aliphatic groups can be saturated or unsaturated and straight or branched chain. Thus, they are primary or secondary aliphatic amines. Such amines include, for example, mono and di-alkyl-substituted amines, mono and di-alkenyl-substituted amines, and amines having one N-alkenyl substituent and one N-alkyl substituent and the like. Examples of cycloaliphatic-substituted aliphatic amines, aromatic-substituted aliphatic amines, and heterocyclic-substituted aliphatic amines, include 2-(cyclohexyl)ethylamine, benzylamine, phenethylamine, and 3-(furylpropyl)amine.

Cycloaliphatic monoamines are those monoamines wherein there is one cycloaliphatic substituent attached directly to the amino nitrogen through a carbon atom in the cyclic ring structure. Examples of cycloaliphatic monoamines, include cyclohexylamines, cyclopentylamines, cyclohexenylamines, cyclopentenylamines, N-ethyl-cyclohexylamine, dicyclohexylamines, and the like. Examples of aliphatic-substituted, aromatic-substituted, and heterocyclic-substituted, and heterocyclic-substituted cycloaliphatic monoamines include propyl-substituted cyclohexyl-amines, phenyl-substituted cyclopentylamines, and pyranyl-substituted cyclohexylamine.

Aromatic amines suitable include those monoamines wherein a carbon atoms of the aromatic ring structure is attached directly to the amino nitrogen. The aromatic ring will usually be a mononuclear aromatic ring (i.e., one derived from benzene) but can include fused aromatic rings, especially those derived from naphthalene. Examples of aromatic monoamines include di(para-methylphenyl)amine, naphthyl-amine, N-(n-butyl)aniline, and the like. Examples of aliphatic-substituted, cycloaliphatic-substituted, and heterocyclic-substituted aromatic monoamines are para-ethoxyaniline, para-dodecylaniline, cyclohexyl-substituted naphthylamine, and thienyl-substituted aniline.

Polyamines suitable herein are aliphatic, cycloaliphatic and aromatic polyamines analogous to the above-described monoamines except for the presence within their structure of another amino nitrogen. The other amino nitrogen can be a primary, secondary or tertiary amino nitrogen. Examples of such polyamines include N-amino-propyl-cyclohexylamines, N,N'-di-n-butyl-paraphenylene diamine, ortho-phenylene diamine, bis-(paraaminophenyl)methane, 1,4-diaminocyclohexane, and the like.

As used herein, the terminology "heterocyclic mono and polyamine(s)" is intended to describe those heterocyclic amines containing at least one primary or secondary amino group. There is also included in the present invention heterocyclic mono and polyamines having at least one primary or secondary amino group. A hetero-N atom in the ring can be a tertiary amino nitrogen; that is, one that does not have hydrogen attached directly to the ring nitrogen. Heterocyclic amines can be saturated or unsaturated and can contain various substituents such as nitro, alkoxy, alkylthio, alkyl, alkenyl, aryl, alkaryl, or aralkyl substituents. Generally, the total number of carbon atoms in the substituents will not exceed about 20. Heterocyclic amines can contain hetero atoms other than nitrogen, especially oxygen and sulfur. Obviously they can contain more than one nitrogen hetero atom. The five and six membered heterocyclic rings are preferred.

Among the suitable heterocyclics are aziridines, azetidines, azolidines, tetra and di-hydro pyridines, pyroles, indoles, piperidines, imidazoles, tolyltriazoles, di and tetrahydroquinolines, di and tetra hydroimidazoles, piperazines, isoindoles, purines, morpholines, thiomorpholines, N-aminoalkylmorpholines, N-aminoalkylthiomorpholines, N-aminoalkylpiperazines, N,N'-di-aminoalkylpiperazines, azepines, azocines, azonines, azecines and tetra, di and perhydro derivatives of each of the above and mixtures of two or more of these heterocyclic amines. Heterocyclic amines are the saturated 5- and 6 membered heterocyclic amines containing only nitrogen, oxygen and/or sulfur in the hetero ring, such as the piperidines, piperazines, thiomorpholine, morpholines, pyrrolidines, and the like. Piperidine, aminoalkylsubstituted piperidines, piperazine, aminoalkyl-substituted piperazines, morpholine, aminoalkyl-substituted morpholines, pyrrolidine, and aminoalkyl-substituted pyrrolidines are also useful herein. Usually the aminoalkyl-substituents are substituted on a nitrogen atoms forming a part of the hetero ring. Specific examples of such heterocyclic amines include N-amino-propylmorpholine, N-aminoethylpiperazine, and N,N'-diaminoethylpiperazine.

Hydroxyamines both mono and polyamines, analogous to those described above are also useful provided they contain at least one primary or secondary amino group. Hydroxy-substituted amines having only tertiary amino nitrogen such as in tri-hydroxyethyl amine, are thus excluded. The hydroxy-substituted amines contemplated are those having hydroxy substituents bonded directly to a carbon atom other than a carbonyl carbon atom; that is, they have hydroxy groups capable of functioning as alcohols. Examples of such hydroxy-substituted amines include ethanolamine, di-(3-hydroxypropyl)-amine, 3-hydroxylbutylamine, 4-hydroxybutylamine, diethanolamine, di-(2-hydroxypropyl)amine, N-(hydroxypropyl)propylamine, N-(2-hydroxyethyl)cyclohexylamine, 3-hydroxycyclopentylamine, para-hydroxyamine, N-hydroxyethyl piperazine, and the like.

A group of amines which may be useful herein are branched polyalkylene polyamines. The branched polyalkylene polyamines are polyalkylene polyamines wherein the branched group is a side chain containing on the average at least one nitrogen bonded alkylene such as $(H_2NR(NHR)_x-)$ where R is the alkylene group, x is a number from 1–100, preferably from 2–10 and R is the alkylene group. The molecule as previously described may also be formulated to contain tertiary nitrogen atoms in the main backbone giving a plurality of primary amine groups connected through an alkylene linkage to the tertiary nitrogen. Further amines useful herein and including a disclosure of the amines previously discussed are found in U.S. Pat. No. 4,234,435 to Meinhardt et al, issued Nov. 18, 1980. The Meinhardt and Davis patent which is assigned to The Lubrizol Corporation is herein incorporated by reference.

It is higholy desired herein that when a phenylamine is employed that it is a mono or dialkyl diphenylamine. Typically, the alkyl portion of the molecule has from 2–16 carbon atoms, preferably 4 to 12 carbon atoms and most preferably 6 to 18 carbon atoms per alkyl group. The dialkyl compounds are preferred in the compositions of the invention.

The alkylated diphenylamines may be prepared as follows.

EXAMPLE 1

A mixture of 169 grams (1.0 mol) of diphenylamine, 504 grams (4.0 mols) of a mixture of isomeric nonenes, 55 grams of Filtrol clay No. 22 and 1.5 grams of concentrated sulfuric acid was stirred for 4 hours at 185°–190° C. in a 0.5 gallon autoclave. The isomeric nonenes employed were derived from the polymerization of propylene, consisting predominantly of secondary olefins, the major portion being dimethyl heptenes, and the ratio of isomers containing internal to those containing terminal double bonds being approximately 2:1. The Filtrol clay No. 22 is an acid activated bleaching earth sold by the Filtrol Corporation having a particle size of 100% through 100 mesh, 90% through 200 mesh and 75% through 325 mesh, a particle density of 1.3 grams per cubic centimeter, a surface area (by nitrogen adsorption) of 275 square meters per gram, and having a chemical analysis on a volatile-free, oxide basis as follows: 70.9% $SiO_2$, 17% $Al_2O_3$, 3.9% $Fe_2O_3$, 3.2% MgO, 1.6% CaO, 2.0% $SO_3$, 1% $K_2O+Na_2O$, and 0.6% $TiO_2$.

During the reaction, the autogenous autoclave pressure was about 200 KPa (33 p.s.i.g.). After the 4 hour reaction period a small sample (10% of the mixture) was taken, filtered, neutralized with anhydrous sodium carbonate and distilled to remove unreacted nonene. The residue was filtered and analyzed by infrared analysis and shown to contain 8.5% free diphenylamine. The alkylated portion consisted of a mixture of p-mono and p,p'-dinonylated diphenylamine. Forty-seven grams (0.45 mol) of styrene was added to the reaction mixture in the autoclave without distilling off excess nonene and stirred for 1 hour at 185°–190° C. at approx. 33 p.s.i.g. autogenous autoclave pressure. After cooling, the reaction mixture was filtered, 10 grams of anhydrous sodium carbonate was added to the filtrate and distilled up to 200° C. pot temperature to remove unreacted nonene. The mixture was then steam distilled at 130°–140° C. to remove olefin polymer. The dry distillation residue was filtered to remove inorganic salts and 344 grams of final product was obtained consisting of a yellow oil with a specific gravity of 0.95. Infrared analysis of the product showed a content of 3.7% nitrogen and 2.2% free diphenylamine. The average number of nonyl substituents per molecule of diphenylamine was 1.65.

EXAMPLE 2

A mixture of 169 grams (1.0 mol) diphenylamine, 392 grams (4.0 mols) of isomeric heptenes, 55 grams of the acid activated clay employed in Example 1, and 1.5 cubic centimeters of concentrated sulfuric acid was stirred for 4 hours at 185°–190° C. in 0.5 gallon autoclave; the autogenous pressure was 80–100 p.s.i.g. The isomeric heptenes employed consisted primarily of secondary heptenes and tertiary heptenes having internal double bonds. Analysis of a sample (10% of total mixture) after the initial four hour reaction period showed a content of unreacted diphenylamine of approximately 7%.

Forty-seven grams (0.45 mol) of styrene was added to the crude alkylate in the autoclave and stirred for one hour at 185°–190° C. at 490–510 KPa (75–80 p.s.i.g.) autogenous autoclave pressure. After cooling, the reaction mixture was filtered, neutralized with anhydrous sodium carbonate and distilled up to 200° C. pot temperature to remove unreacted heptene, after which it was steam distilled at 130°–135° C. to remove olefin polymer and then filtered.

Three hundred ten grams of heptylated, styrene scavenged diphenylamine was obtained. It was a clear, pale yellow oil. Analysis of the product using infrared absorption show that the product contained 2.15% free diphenylamine. The average number of heptyl substituents per molecule was 1.9.

EXAMPLE 3

A mixture of 169 grams (1 mol) of diphenylamine, 55 grams of the acid activated clay employed in Example 1, 1.4 milliliters of concentrated sulfuric acid, and 448 grams (4 mols) of isomeric octenes is heated and stirred for 4 hours at 185°–190° C. in an autoclave. The autogenous pressure during the reaction was approx. 380 KPa (60 p.s.i.g.). The isomeric octenes employed consist predominantly of secondary octenes and tertiary octenes having internal double bonds.

The hot autoclave is vented through a condenser and most of the excess octene was distilled off. At this point the crude alkylate contained approx. 7% unreacted diphenylamine, and approx. 7% mono-tertiary butyl diphenylamine.

To the residue in the autoclave is added 224 grams (2 mols) of diisobutylene and stirring was again continued for 1 hour at 180°–185° C. under an autogenous pressure of approx. 60 p.s.i.g. The diisobutylene employed was obtained by the polymerization of isobutylene and consisted of approximately 75% 2,4,4-trimethyl pentene-1, 23% 2,4,4-trimethyl pentene-2 with about 2% of other octene isomers.

After cooling, the reaction mixture is filtered, neutralized with anhydrous sodium carbonate and distilled up to 200° C. pot temperature to remove residual unreacted octene, and then steam distilled to distill off any olefin polymer. The warm product is dried by blowing with dry nitrogen and the sodium carbonate is removed by filtration. 357.5 grams of a light brown colored liquid product was obtained containing 1.5% diphenylamine and 1.2% mono-tertiary butyl diphenylamine.

The reactive hydrogens in the amine determine the number of equivalents present. For the purposes of the present invention a monofunctional secondary amine (monoamine) contains a single equivalent of amine hydrogen, while a monofunctional primary amine contains two equivalents. An amine containing one of each tertiary amine structure, a secondary amine structure and a primary amine structure contains three equivalents of that compound.

It is particularly preferred that the amine group be used to cap the beta-thiodialkanol. That is, the amine should be at both ends of the beta-thiodialkanol or the beta-thiodialkanol polymer. Thus, to prevent further polymerization, it is desired that the monofunctional secondary amine be employed.

The second component of the present invention is a beta thiodialkanol.

The products of the present invention are prepared by reacting a beta-thiodialkanol as shown in Formula I with an amine. Preferably, capping is done at both ends of the beta-thiodialkanol by using two equivalents of the amine. The beta-thiodialkanol may be the monomer or a polymeric form $$HO[R^1(S)_xR^2]_yOR^1(S)_xR^2OH \qquad III$$

where y is conveniently 1 to 7, or mixtures of the monomer and polymer.

Variations are also possible in the preparation of the compositions of the present invention such as by introducing limited quantities of the amine and polymerizing the beta-thiodialkanol monomer onto the amine and then capping that reaction product with another mole of the amine. The preferred method, however, is that of reacting the beta-thiodialkanol and the amine in the same pot.

The reaction is typically conducted in the presence of a catalytic amount of acids, such as sulfuric, phosphoric or para-toluene sulfonic acids. The catalyst level is typically at 0.5-3% by weight of the betathiodialkanol and at temperatures of about 50°-250° C. Conveniently, an inert solvent such as toluene is utilized under refluxing conditions in the condensation reaction. A further discussion of the preparation of such betathiodialkanols is found in the Woodward article previously incorporated by reference.

The reaction is conveniently conducted until no more water is formed. Water is evolved from both the polymerization and capping reactions. Typically, the time period will be about 2 to about 10 hours to complete the reaction. At that time, the catalyst is neutralized with sodium hydroxide or other suitable base. The solvent is then removed under reduced pressure and filtered. The yield will vary between 70% and 100% depending upon the individual reaction conditions.

The beta-thiodialkanol as previously described is of the formula $HOR^1(S)_xR^2OH$ (I) and allows for substantially any group of substituents between the hydroxyl group and the sulfur provided that two carbon atoms intervene between the sulfur and the oxygen.

In a preferred state $R^1$ and $R^2$ are each $-CHR^3CHR^4-$. Where both $R^3$ and $R^4$ are hydrogen, an ethylene group exists. Of course, $R^3$ and $R^4$ may be any non-interfering hydrocarbyl group. A hydrocarbyl group as defined herein is a moiety containing hydrogen and carbon and any other non-interfering atoms. Preferably $R^3$ or $R^4$ are limited to lower straight chain alkyl groups such as methyl or ethyl. It is noted, that if a t-butyl group is inserted in the molecule as $R^3$ or $R^4$ that the condensation reaction to form the polymer is particularly hindered. However, a styrene residue is non-interfering and may be used as $R^1$ or $R^2$.

The beta-thiodialkanol preferably contains only one sulfur atom per repeating unit, i.e., x is 1. However, it is acceptable and under some conditions desirable to have x at a value of 2 thereby having a disulfide structure in the molecule. It is also possible to have compositions where there are mixtures of monosulfide and disulfide. For an automatic transmission fluid, the monosulfide is desired. In lubricating oils for engines, some disulfide is desired for anti-wear.

The reaction of the amine and the thiodialkanol may be simply carried out by mixing all of the ingredients in a single pot in the required proportions and initiating the reaction. Where it is desired to obtain a material which contains a single unit of the thiodiglycol it is desired to introduce the amine to the pot and to slowly add the thiodiglycol. That is, if the entire amount of thiodiglycol is placed in the pot the auto condensation of that material to form a homopolymer competes with the capping reaction by the amine. It is also possible in the present invention to obtain a variety of polymers of the thiodiglycol by allowing the auto condensation to proceed to varying degrees and then to cap the respective polymers with the amine. It is of course further possible to blend such products thereby obtaining a nearly exact distribution of the desired degree of the homopolymer within the desired end product.

Conveniently, two equivalents of the amine react with two equivalents of the beta-thiodiglycol, e.g., one equivalent of thiodiglycol is one-half the molecular weight. However, any number of excess equivalents of the beta-thiodiglycol may be used, especially 4 to 10 equivalents per two equivalents of amine.

The materials of the present invention as previously stated are desirably utilized in various hydraulic and lubricating compositions. The compositions, when employed in a motor oil, are conveniently used in a minor amount with a major amount of a base fluid.

The base fluid for an aqueous based composition is simply water and such other components as are necessary for the desired functional aspects of the fluid. Where the desired end product is a lubricating oil or a transmission fluid, the base oil is typically hydrocarbon in nature. Disclosed below are typical hydrocarbon oils useful in conjunction with the compositions of the present invention.

Unrefined, refined and rerefined oils (and mixtures of each with each other) of the type disclosed hereinabove can be used in the lubricants and functional fluids of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

The synthetic lubricating oils useful herein include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodceylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of about 100, diphenyl ether of polyethylene glycol having a molecular weight of about 500–1000, diethyl ether of polypropylene glycol having a molecular weight of about 1000-±500, etc. or mono- and polycarboxylic esters thereof, for example, the acetic acid esters, mixed $C_3$–$C_8$ fatty acids esters, or the $C_{13}$Oxo acid diester of tetraethylene glycol.

Another suitable class of synthetic lubricating oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)-sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy- or polyaryloxy-siloxane oils and silicate oils comprise another useful class of synthetic lubricants (e.g., tetraethyl silicate, tetraisopropyl silicate tetra-(2-ethylhexyl)silicate, tetra-(4-methyl-hexyl)silicate, tetra-(p-tert-butylphenyl)silicate, hexyl-4-methyl-2-pentoxy)-disiloxane, poly(methyl)siloxanes, poly(methylphenyl)-siloxanes, etc.). Other synthetic lubricating oils include liquid esters of phosphorus containing acids (e.g., tricresyl phosphate, trioctyl phosphate, diethyl ester of decane phosphonic acid, etc.), polymeric tetrahydrofurans and the like.

Polyolefin oligomers are typically formed by the polymerization reaction of alpha-olefins. Nonalpha olefins may be oligomerized to give a synthetic oil within the present invention, however, the reactivity and availability of alpha-olefins at low cost dictates their selection as the source of the oligomer.

The polyolefin oligomer synthetic lubricating oils of interest in the present invention include hydrocarbon oils and halo-substituted hydrocarbon oils such as are obtained as the polymerized and interpolymerized olefins, e.g., oligomers, include the polybutylenes, polypropylenes, propylene-isobutylene copolymers, chlorinated polybutylenes, poly(1-hexenes), poly(1-octenes), poly(1-decenes), similar materials and mixtures thereof.

Typically, the oligomer is obtained from a monomer containing from about 6 to 18 carbon atoms. Most preferably, the monomer used to form the oligomer is decene, and preferably 1-decene. The nomenclature alpha-olefin is a trivial name and the IUPAC nomenclature of a 1-ene compound may be considered to have the same meaning within the present invention.

While it is not essential that the oligomer be formed from an alpha-olefin, such is desirable. The reason for forming the oligomer from an alpha-olefin is that branching will naturally occur at the points where the olefin monomers are joined together, and any additional branching within the backbone of the olefin can provide too high a viscosity of the end oil. IT is also desirable that the polymer formed from the alpha olefin be hydrogenated. The hydrogenation is conducted according to known practices. By hydrogenating the polymer, free radical attack on the allyic carbons remaining after polymerization is minimized.

The molecular weight of the oligomer typically averages from about 250 to about 1400, conveniently from about 280 to about 1200, preferably from about 300 to about 1100, and most preferably about 340 to about 520. The choice of molecular weight of the oligomer is largely dependent upon whether a viscosity improver is included within the formulation. That is, the polyolefin oligomer, may require either a thickening or a thinning effect to ensure that the proper lubricating viscosities are maintained under extreme heat and cold conditions.

A further desirable synthetic lubricant is an alkylated aromatic compound. The alkylated aromatic compounds are particularly beneficial in improving the low temperature flow characteristics. A particularly useful synthetic lubricant is a mixture of the alpha olefin oligomer and the alkylated aromatic. Typically, a mixture of the oligomer to the alkylated aromatic will be at a weight ratio of about 8:1 to about 1:8.

Materials which also also be included herein are the natural oils. Natural oils include animal oils and vegetable oils (e.g., castor oil, lard oil) as well as the previously described oils.

Additional materials which are desirably added to the hydrocarbon based fluids are as follows: Viscosity improving materials may be included in the compositions of the present invention. The viscosity index improvers typically include polymerized and copolymerized alkyl methacrylates and mixed esters of styrene-maleic anhydride interpolymers reacted with nitrogen-containing compounds.

Polyisobutylene compounds are also typically used as viscosity index improvers. The amount of viscosity improver which may be typically added to the fully formulated transmission fluid composition is about 1% to about 50%, preferably about 10% to about 25% by weight.

Zinc salts are also added to transmission lubricants. Zinc salts are ordinarily utilized as extreme pressure agents, such as zinc dithiophosphates. The zinc salts are added at levels measured by weight of the zinc metal at from about 0.02% to about 0.2%, preferably from about 0.04% to about 0.15% by weight.

Additional ingredients which may be included in a transmission fluid are fatty acid amides which are useful as additional friction modifiers, particularly for reducing the static coefficient of friction. Further useful components herein include seal swell agents such as sulfones and sulfolanes. Suitable seal swell agents are disclosed in U.S. Pat. No. 4,029,587 to Koch issued June 14, 1977. A still further useful component in the present invention is a foam suppression agent such as a silicone oil. Any other typical ingredient may be included herein such as pour point depressants, dyes, odorants and the like.

Additional components which are typically used in transmission fluids, motor oils or hydraulic fluids include the following.

Extreme pressure agents and corrosion and oxidation-inhibiting agents which may be included in the compositions of the invention are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents and corrosion-oxidation inhibitors also serve as anti-wear agents. Zinc dialkylphosphorodithioates are a well known example.

Anti-wear agents that are particularly useful in the compositions of the invention are those obtained from a phosphorus acid of the formula $(R'O)_2PSSH$, wherein each $R'$ is independently a hydrocarbon-based group, or the phosphorus acid precursors thereof with at least one phosphite of the formula $(R''O)_3P$, $R''$ is a hydrocarbon-based group, under reaction conditions at a temperature of about 50° C. to about 200° C. $R'$ is preferably an alkyl group of about 3 to about 50 carbon atoms, and $R''$ is preferably aromatic. The salt is preferably a zinc salt, but can be a mixed salt of at least one of said phosphorus acids and at least one carboxylic acid. These anti-wear agents are described more fully in U.S. Pat. No. 4,263,150, which is incorporated herein by reference. These anti-wear agents as well as the anti-wear agents referred to above can be provided in the compositions of the invention at levels of about 0.1% to about 5%, preferably about 0.25% to about 1% by weight based on the total weight of said fluid compositions.

Additional oxidation inhibitors that are particularly useful in the fluid compositions of the invention are the hindered phenols (e.g., 2,6-di-(t-butyl)phenol); aromatic amines (e.g., alkylated diphenyl amines); alkyl polysulfides; selenides; borates (e.g., epoxide/boric acid reaction products); phosphorodithioic acids, esters and/or salts; and the dithiocarbamates (e.g., zinc dithiocarbamates). These oxidation inhibitors as well as the oxidation inhibitors discussed above are preferably present in the fluids of the invention at levels of about 0.025% to about 5%, more preferably about 0.1 to about 2% by weight based on the total weight of such compositions.

The rust-inhibitors that are particularly useful in the compositions of the invention are the alkenyl succinic acids, anhydrides and esters, preferably the tetrapropenyl succinic acids, acid/esters and mixtures thereof; metal (preferably calcium and barium) sulfonates; the amine phosphates; and the imidazolines. These rust-inhibitors are preferably present at levels of about 0.01% to about 5%, preferably about 0.02% to about 1% by weight based on the total weight of the product.

Pour point depressants may be included in the compositions described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co. Publishers, Cleveland, Ohio 1967).

Examples of useful pour point depressants are polymethylacrylates; polyacrylates; polyacrylamides; condensation products of haloparaffin waxes and aromatic compounds; vinyl carboxylate polymers; and terpolymers of dialkylfumarates, vinyl esters of fatty acids and alkyl vinyl ethers. Pour point depressants useful for the purposes of this invention, techniques for their preparation, and their uses are described in U.S. Pat. Nos. 2,387,501; 2,015,748; 2,655,479; 1,815,022; 2,191,498; 2,666,746; 2,721,877; 2,721,878 and 3,250,715 which are hereby incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Kerner (Noyes Data Corporation, 1976), pages 125–162.

UTILIZATION OF THE COMPOSITION

The composition of the present invention is typically used in the automatic transmission fluid, hydraulic fluid, functional fluid or lubricating oil composition at a level of about 0.025% to about 5%, preferably from about 0.1% to about 2% by weight. As the products of the invention are oleophilic, the blending of the products is relatively simple. Where the compositions of the present invention are intended for use in an aqueous based material, it is desirable to include such adjuvants and other materials as may be necessary to stably disperse the active ingredients in the aqueous formulation. When an aqueous composition is utilized, it is typically up to 85% and preferably up to 90% water, with the remainder being the active ingredient of this invention and other materials typically placed in such aqueous formulations.

A particular advantage of the compositions of the present invention is that they have excellent free radical trapping and peroxide decomposing properties within a single molecule. The compositions of the present invention are easily blended into an automatic transmission fluid or motor oil.

The following are examples of the present invention.

EXAMPLE I

Two moles of diphenylamine and 300 grams of toluene solvent are combined in a suitable reaction flask. The reaction mixture is placed under a nitrogen flow and 3 grams of para-toluene sulfonic acid catalyst are added to the reaction mixture. The reaction is heated to reflux temperature. Thereafter, one mole of thiodiethanol is added dropwise to the reaction mixture over a period of two hours. The water of reaction is removed through the use of a trap. The reaction is continued until no more water is evolved.

The catalyst is then neutralized with a 50% aqueous sodium hydroxide solution. The solvent is removed under reduced pressure and the product is filtered at 80° C. The filtrate solidified at room temperature (20° C.). The product is isolated in 93% yield.

EXAMPLE II

To a suitable reaction flask are combined one mole of n-dodecyl amine, two moles of phenothiazine, 4 moles of thiodiglycol and 200 mls. of xylene solvent. The reaction mixture is heated to reflux and thereafter 6 grams of sulfuric acid catalyst are added to the reaction mixture. The reaction mixture is then raised to a temperature of 240° C. through distillation of the solvent. The reaction mixture is held at 240° C. until no further water is evolved. The water is collected in a trap as it is evolved.

Sufficient 50% aqueous sodium hydroxide is added to neutralize the catalyst. The solvent is removed from the reaction mixture at reduced pressure and the product is filtered at 50° C.

EXAMPLE III

Two moles of phenothiazine which is dinonyl-substituted on the aromatic rings is added to a suitable reaction flask. To the reaction flask are then added 3 moles of thiodiethanol, 5 grams of sulfuric acid catalyst, and 400 mls. of toluene. The reaction is heated under reflux until no further water is evolved.

The catalyst is then neutralized with 50% aqueous sodium hydroxide and the solvent removed by distillation under reduced pressure. The product is then filtered at 50° C. and the filtrate is the product.

EXAMPLE IV

Three automatic transmission fluids are obtained which do not contain conventional antioxidants. The three automatic transmission fluids A, B and C are then separately treated with each of the antioxidants of Examples I–III. The treatment level with each of the antioxidants is at 1 part of the antioxidant per 100 parts of the automatic transmission fluid.

A fourth automatic transmission fluid (D) is obtained and treated at 100 parts with 0.5 parts of the antioxidant of Example I and 0.5 parts of the antioxidant of Example II.

It is observed that products A–D all perform in an exemplary fashion as automatic transmission fluids which are not overly sensitive to oxidation.

What is claimed is:

1. A composition of matter which is the amine terminated reaction product obtained from two equivalents of a secondary aromatic monoamine with two equivalents of a beta-thiodialkanol.

2. The composition of claim 1 wherein the beta-thiodialkanol is thiodiglycol.

3. The composition of claim 1 wherein the amine is a ring-alkylated diphenylamine.

4. The composition of claim 1 wherein the beta-thiodialkanol is a disulfide.

5. The composition of claim 3 wherein the alkylated diphenylamine is a ring-dialkylated diphenylamine.

6. The composition of claim 1 wherein the amine is phenothiazine or a phenothiazine derivative.

7. The composition of claim 1 wherein the amine is an aromatic amine and the beta-thiodialkanol is a disulfide.

8. A lubricating composition comprising a major amount of an oil of lubricating viscosity and a minor amount of the composition of claim 1.

9. A composition according to claim 1 in an automatic transmission fluid.

10. A composition produced by the reaction of at least two equivalents of a primary or a secondary amine, or mixtures thereof, provided the amines contain at least one straight or branched aliphatic group of 4 or more carbon atoms, with at least two equivalents of a beta-thiodialkanol.

11. The composition of claim 10 wherein the reaction product is amine terminated.

12. The composition of claim 10 wherein the reaction product is oil-soluble.

13. The composition of claim 10 wherein the beta-thiodialkanol is thiodiglycol.

14. The composition of claim 10 wherein the amine is an aromatic amine.

15. The composition of claim 10 wherein the beta-thiodialkanol is a disulfide.

16. The composition of claim 10 wherein at least one amine is a diphenylamine or an alkylated diphenylamine.

17. The composition of claim 10 wherein at least one amine is phenothiazine or a phenothiazine derivative.

18. The composition of claim 10 wherein the amine is a secondary amine.

19. A lubricating composition comprising a major amount of an oil of lubricating viscosity and a minor amount of the composition of claim 10.

20. The composition of claim 10 in an automatic transmission fluid.

21. A composition which is the amine terminated reaction product of two equivalents of an aliphatic ring-substituted aromatic amine with two equivalents of a beta-thiodialkanol.

22. The composition of claim 21 wherein the beta-thiodialkanol is a disulfide.

23. The composition of claim 21 wherein the amine is an alkylated diphenylamine.

24. The composition of claim 23 wherein the alkylated diphenylamine is a dialkylated diphenylamine.

25. The composition of claim 21 wherein the amine is a phenothiazine derivative.

26. The composition of claim 21 wherein the amine contains from about 4 to about 18 aliphatic carbon atoms.

27. A lubricating composition comprising a major amount of an oil of lubricating viscosity and a minor amount of the composition of claim 21.

28. The composition of claim 21 in an automatic transmission fluid.

* * * * *